United States Patent
Kao et al.

(10) Patent No.: US 10,896,502 B2
(45) Date of Patent: Jan. 19, 2021

(54) PREDICTION SYSTEM, METHOD AND COMPUTER PROGRAM PRODUCT THEREOF

(71) Applicant: China Medical University Hospital, Taichung (TW)

(72) Inventors: Chia-Hung Kao, Taipei (TW); Shang-Wen Chen, Taipei (TW); Wei-Chih Shen, Taichung (TW); Kuo-Chen Wu, Taichung (TW)

(73) Assignee: CHINA MEDICAL UNIVERSITY HOSPITAL, Taichung (TW)

( * ) Notice: Subject to any disclaimer, the term of this patent is extended or adjusted under 35 U.S.C. 154(b) by 23 days.

(21) Appl. No.: 16/396,908

(22) Filed: Apr. 29, 2019

(65) Prior Publication Data
US 2020/0202516 A1 Jun. 25, 2020

(30) Foreign Application Priority Data
Dec. 20, 2018 (TW) .............................. 107146171 A

(51) Int. Cl.
*G06T 7/00* (2017.01)
*G16H 50/20* (2018.01)
*G06N 3/08* (2006.01)

(52) U.S. Cl.
CPC ............. *G06T 7/0012* (2013.01); *G06N 3/08* (2013.01); *G16H 50/20* (2018.01); *G06T 2207/30096* (2013.01)

(58) Field of Classification Search
CPC ......... G06T 7/0012; G06T 2207/30096; G06T 2207/20081; G06T 2207/20084; G06T 2207/30081; G16H 50/20; G16H 50/70; G06N 3/08
USPC ........................................................ 382/128
See application file for complete search history.

(56) References Cited

U.S. PATENT DOCUMENTS

| | | | |
|---|---|---|---|
| 2017/0352157 A1* | 12/2017 | Madabhushi | G06K 9/00147 |
| 2018/0240233 A1* | 8/2018 | Kiraly | G06T 7/0012 |
| 2019/0030371 A1* | 1/2019 | Han | G06N 3/08 |
| 2019/0122073 A1* | 4/2019 | Ozdemir | A61B 6/5217 |
| 2019/0156954 A1* | 5/2019 | Madabhushi | G16B 50/30 |
| 2019/0206056 A1* | 7/2019 | Georgescu | G06N 7/005 |
| 2019/0209116 A1* | 7/2019 | Sjostrand | A61B 6/5223 |
| 2019/0223789 A1* | 7/2019 | Wang | A61B 5/055 |

FOREIGN PATENT DOCUMENTS

| | | |
|---|---|---|
| CN | 108694718 A | 10/2018 |
| CN | 109003672 A | 12/2018 |

* cited by examiner

*Primary Examiner* — Ali Bayat
(74) *Attorney, Agent, or Firm* — Bacon & Thomas, PLLC

(57) ABSTRACT

A prediction system of tumor image-aided prediction of prognosis for patients with uterine cervical cancer is provided. The prediction system includes a data augmentation module and a deep convolution neural network model. The data augmentation module is used to apply a data expansion process of the image data, so as to generate a plurality of slice sets of the uterine cervical cancer tumor. The deep convolution neural network model is used to apply a feature analysis to the slices, so as to predict the prognosis of a patient after chemoradiotherapy.

9 Claims, 8 Drawing Sheets

PREDICTION SYSTEM, METHOD AND COMPUTER PROGRAM PRODUCT THEREOF

CROSS REFERENCE TO RELATED APPLICATION

This application claims the benefits of the Taiwan Patent Application Serial Number 107146171, filed on Dec. 20, 2018, the subject matter of which is incorporated herein by reference.

BACKGROUND OF THE INVENTION

1. Field of the Invention

The present invention belongs to the field of image-aided prediction technology, and in particular, a deep learning of tumor image-aided prediction of prognosis for patients with uterine cervical cancer system, method and computer program product thereof.

2. Description of Related Art

Currently, chemoradiotherapy is the standard treatment for locally advanced uterine cervical cancer, but the prognosis (such as local tumor control, distant metastasis, or survival) for these patients is not satisfactory enough. Since the treatment may cause many side effects, the quality of patient care can be effectively improved if the prognosis before the treatment is predictable.

Nowadays, Positron Emission Tomography (PET)/Computed Tomography (CT) of fludeoxyglucose (18F-FDG) has been widely used to evaluate a pre-treatment staging of uterine cervical cancer, and some research methods use features inferred from images to predict the possibility of treatment response, local recurrence, or distant metastasis.

However, the prediction technique combining PET/CT radiomics, traditional machine learning and statistical algorithms still has a flaw in accuracy. As a result, the risk of prediction error is high.

In view of this, the present invention provides an improved deep learning of image-aided prediction system, method and computer program product thereof to effectively address aforementioned problems.

SUMMARY OF THE INVENTION

The present invention provides a deep learning system of tumor image-aided prediction of prognosis for patients with uterine cervical cancer, which is formed on the basis of deep learning algorithm and accompanied by the training of tumor images. The present invention may establish a deep convolution neural network model by deep learning, and the model may analyze an image of a uterine cervical tumor, thereby predicting the prognosis of the patient after receiving concurrent chemoradiotherapy. The present invention improves the accuracy of prediction through the operation of the deep convolution neural network.

According to an aspect of the present invention, there is provided a prediction system used to analyze the image data of a uterine cervical tumor before treatment. The prediction system comprises a data augmentation module and an analysis module. (The data augmentation module may perform data expansion process on the image data to generate a plurality of slice sets. The slice set is the basic unit of data used in the analysis. The analysis module may perform feature analysis on the slice sets through a deep convolution neural network model to predict the prognosis.

According to another aspect of the present invention, a prediction method is provided to analyze huge image data of the tumor. The method comprises two major steps: performing a data expansion process on the image data through a data augmentation module to generate a plurality of slice sets; performing the feature analysis on the slice sets through a deep convolution neural network model to predict the prognosis.

According to another aspect of the present invention, a computer program product stored in a non-transitory computer-readable medium is provided for the operation of a prediction system, wherein the computer program product comprises an instruction enabling the prediction system to perform a data expansion process to generate a plurality of slice sets; and an instruction enabling the prediction system to perform the feature analysis to predict the prognosis.

The objects, advantages, and novel features of the invention will become more apparent from the following detailed description when taken in conjunction with the accompanying drawings.

DETAILED DESCRIPTION OF THE PREFERRED EMBODIMENT

The following specification will provide various embodiments of the present invention. These embodiments are not intended to be limiting. Features of the each embodiments may be modified, substituted, combined, separated and designed to be applied to other embodiments.

Figure 1A:
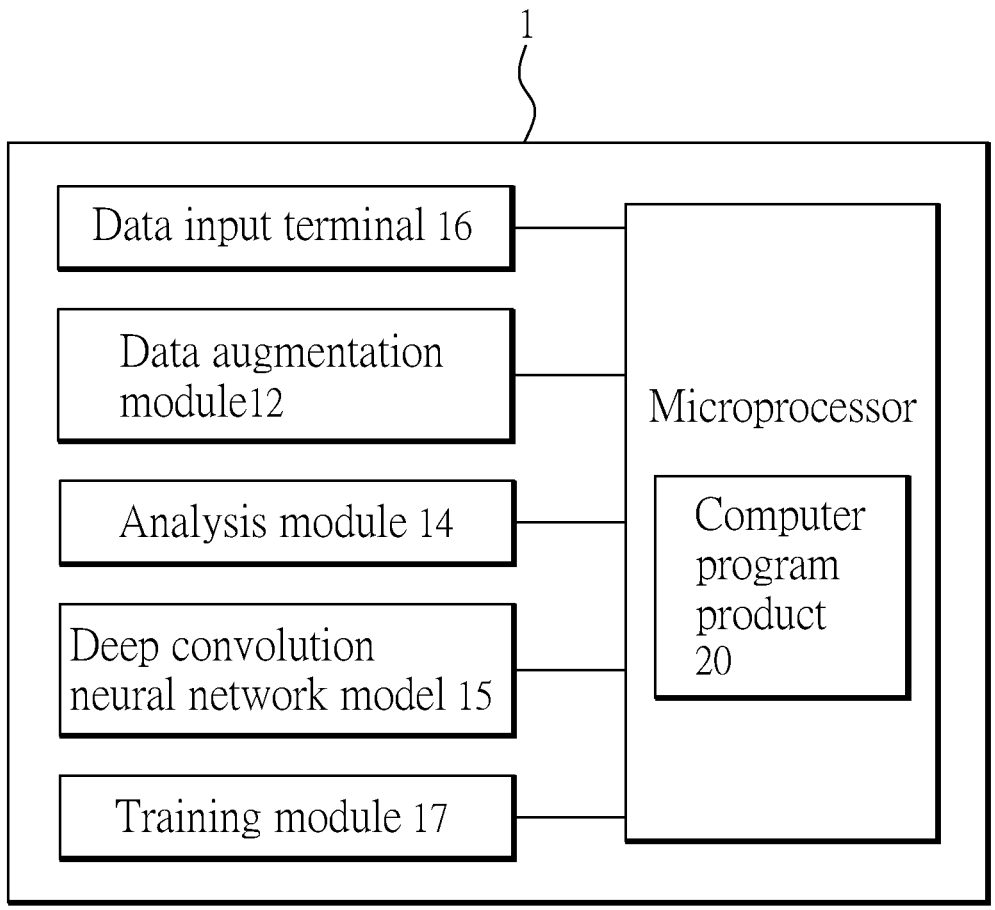
FIG. 1(A) is a system architecture diagram of a deep learning of tumor image-aided prediction of prognosis for patients with uterine cervical cancer system according to an embodiment of the present invention.

FIG. 1(A) is a system architecture diagram of a prediction system 1 (deep learning of tumor image-aided prediction of prognosis for patients with uterine cervical cancer system) according to an embodiment of the present invention. As shown in FIG. 1(A), a deep learning of tumor image-aided prediction of prognosis for patients with uterine cervical cancer system 1 (hereinafter called the "the prediction system 1") comprises a data augmentation module 12, an analysis module 14, and a deep convolution neural network model 15. In an embodiment, the system 1 may further comprise a data input terminal 16 for obtaining external image data, that is, an user may input the image data to the system 1 through the data input terminal 16. Herein, "image" may be, for example, a PET image or CT image of a uterine cervical tumor in a patient before treatment, wherein the treatment may, by way of example and not limitation, be concurrent chemoradiotherapy, and the "image data" may, by way of example and not limitation, be a tumor volume derived from PET or CT images. For clarity, the following paragraph will be exemplified by PET images. In an embodiment, after the system 1 obtains the image data, the data augmentation module 12 may perform a data expansion process on the image data to increase the amount of data with the preservation of a part of 3D information. The analysis module 14 may perform a feature analysis on the expanded slice sets by the deep convolution neural network model 15 (for example, the deep convolution neural network model 15 performs analysis on the image data and uses the feature to establish a prediction path) in order to predict the prognosis of the patient after treatment. For instance, the deep learning of tumor image-aided prediction of prognosis for patients with uterine cervical cancer system 1 can predict the outcome (such as the possibility of local recurrence or distant metastasis) of chemoradiotherapy when a user inputs image data of the uterine cervical tumor, which is taken before the treatment, to the system 1. In addition, the system 1 may further comprise a training module 17 to control the model for training and undergo deep learning. When the model for training finishes its training process, the deep convolution neural network model 15 is formed. Details of each component will be explained below.

The deep learning of tumor image-aided prediction of prognosis for patients with uterine cervical cancer system 1 may be an image processing device, which may be implemented by any device having a microprocessor, such as a desktop computer, a notebook computer, a smart mobile device, a server, a cloud server or the like. In an embodiment, the system 1 may have a network communication function to transmit the data via the network, wherein the network can be a wired or a wireless network, and thus the system 1 can obtain image data through the network. In an embodiment, the system 1 can be implemented by executing a computer program product 20 in a microprocessor. For instance, the computer program product 20 can have a plurality of instructions, and such instructions may enable a processor to execute the functions of the data augmentation module 12, analysis module 14, deep convolution neural network model 15, and training module. In one embodiment, the computer program product 20 can be stored in a non-transitory computer-readable medium, for example, but not limited to, a memory.

In an embodiment, the data input terminal 16 is a physical port for obtaining external data. For example, when the system 1 is implemented by a computer, the data input terminal 16 may, by way of example and not limitation, be a USB interface on a computer, transmission line connector and the like. Moreover, the data input terminal 16 may be integrated with a wireless communication chip, and thus the data can be received by wireless transmission.

The data augmentation module 12 may be a functional module, which can be implemented by a functional code. For instance, the functional code may enable the microprocessor to execute the function of the data augmentation module 12 when the microprocessor, which is located in the system 1, performs the program code. The analysis module is a functional module, which can be implemented by a functional code. For example, the functional code may enable the microprocessor to execute the function of the analysis module 14 when the microprocessor in the system 1 performs the program code. The training module is a functional module, which can be implemented by a functional code. For instance, the functional code may enable the microprocessor to execute a function of said training module 17 when the microprocessor in the prediction system 1, performs the program code. In one embodiment, the training module may be integrated with the deep convolution neural network model 15 (model for training). Various modules described above can be implemented by independent and different programs, or by different subprograms in the same program. In addition, the aforementioned programs can, by way of example and not limitation, also be integrated into the computer program product 20.

The details of the deep convolution neural network model 15 will be explained as follows. The deep convolution neural network model 15 of the present invention is an artificial intelligence using a deep convolution neural network to analyze image features, and is formed by a training process on the basis of deep learning techniques. In one embodiment, the deep convolution neural network model 15 consists of a complex algorithm (such as a program code). Furthermore, to distinguish a pre-training and post-training deep convolution neural network model 15, the pre-training deep convolution neural network model 15 will be referred as "model for training". In an embodiment, the model for training should undergo at least one "training phase" to establish a feature path, and the model for training should undergo at least one "test phase" to test the accuracy of the feature path. Only when the accuracy meets the requirement, the model for training can be used as a deep convolution neural network model 15 for the subsequent use. In the present invention, the model for training will undergo repeated trainings, and it will generate different feature paths after each training. The feature path with the highest accuracy will be set as the feature path of the deep convolution neural network model 15.

Figure 1B:
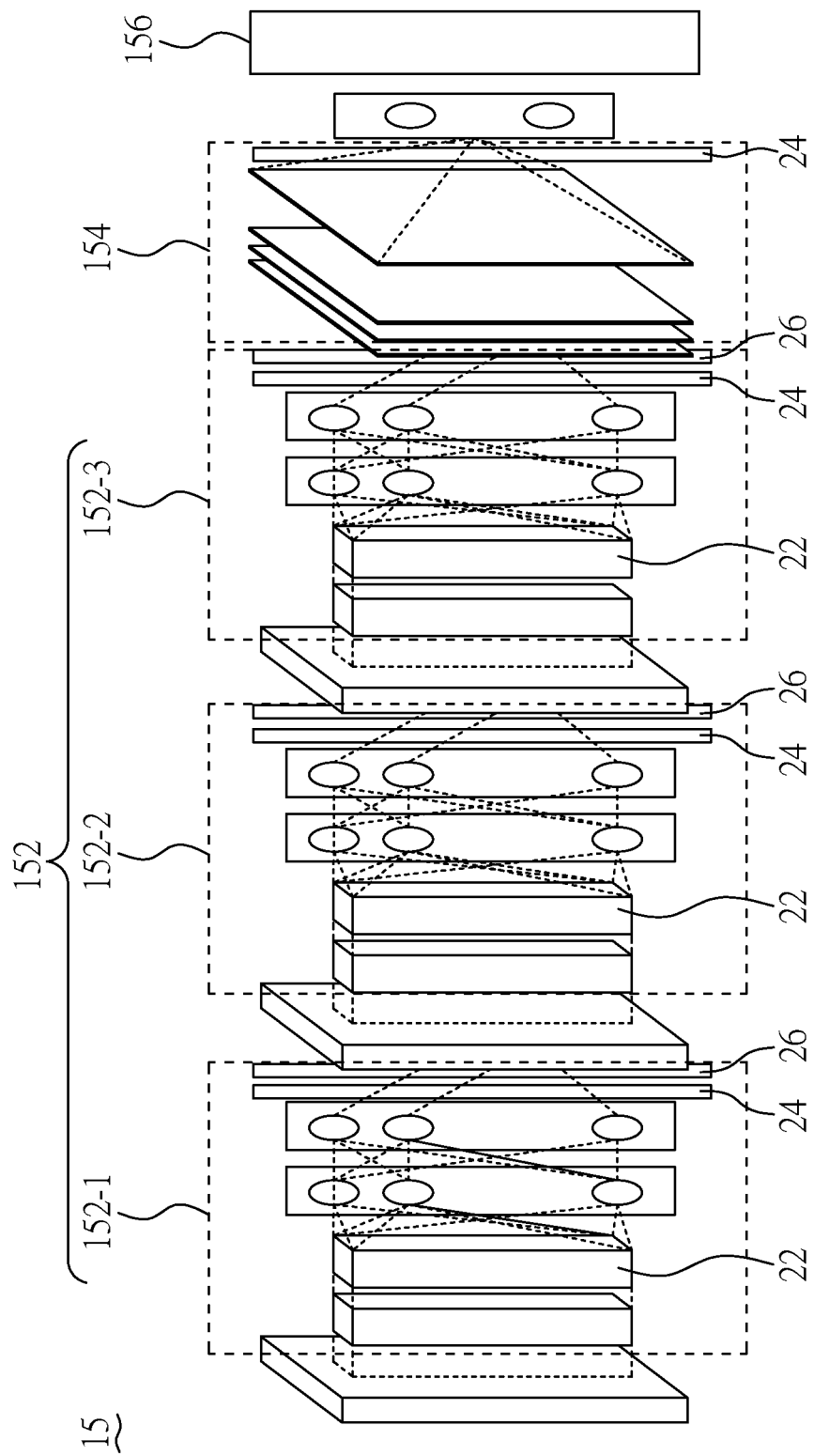
FIG. 1(B) is architecture diagram of a deep convolution neural network model according to an embodiment of the present invention.

FIG. 1(B) is architecture diagram of the deep convolution neural network model 15 according to our design. To predict the possibility of local recurrence or metastasis in patients with uterine cervical tumor, the deep convolution neural network model 15 (or model for training) is configured to comprise a plurality of multiple convolutional layer (mlpconv layer) 152, at least one global average pooling layer 154 and at least one loss function layer 156. The maximum number of the mlpconv layer 152 is determined by the size of a slice. The final number is not greater than the maximum number and determined by the prediction performance. To improve the image resolution, to balance the amount of data for training and operation time, and to avoid the overfitting with decreasing accuracy, the number of the mlpconv layer 152 is 3 and the number of image data for training is 142 PET images. The 142 PET images will generate 1562 slice sets after a data expansion process. It is noted that the deep convolution neural network model 15 described herein is merely an example.

In the present embodiment, an input terminal of the first mlpconv layer 152-1 is used for receiving image data (such as the slice sets expanded by the data augmentation module 12), an output terminal of the first mlpconv layer 152-1 is connected with an input terminal of the second mlpconv layer 152-2, an output terminal of the second mlpconv layer 152-2 is connected with an input of the third mlpconv layer 152-3, an output terminal of the third mlpconv layer 152-3 is connected with an input terminal of a global average pooling layer 154, and an output terminal of the global average pooling layer 154 is connected with a softmax function to predict patient's prognosis. The prediction performance is evaluated by the loss function layer 156.

It is noted that each mlpconv layer 152 is configured to comprise at least one feature detector. In one embodiment, the feature detector is represented in a matrix form, and can execute a convolution operation by a pixel value of each pixel position for image data (for example, a SUV value of each voxel) to obtain features of image data. The initial content of each feature detector is randomly generated, but will be adjusted through the accuracy of training results to improve the training effect. In one embodiment, a feature detector of the first mlpconv layer 152-1 and the original image data input to the model for training undergo the first convolution operation in order to generate a first feature map; a feature detector of the second mlpconv layer 152-2 and the convolution operation result of the first mlpconv layer 152-1 (first feature map) undergo the second convolution operation to generate a second feature map; a feature detector of the third mlpconv layer 152-3 and the convolution operation result of the second mlpconv layer 152-2 (second feature map) undergo the third convolution operation to generate a third feature map. Finally, in the global average pooling layer, each feature map is represented by a value which is the average of all feature coefficients on the map. Thereby, in the image of uterine cervical tumor, important features relating to tumor recurrence or metastasis can be identified.

In an embodiment, each mlpconv layer 152 may respectively comprise a normalization operation unit 22 to execute a normalization operation. Herein, the normalization operation may be Batch normalization, for example. The normalization operation unit 22 can normalize the data of each convolution operation result of the mlpconv layer 152, thereby speeding up the convergence of subsequent data processing and making the training process more stable. In addition, each mlpconv layer 152 may respectively comprise a pooling unit 26 to execute a pooling operation. Herein, the pooling operation will be a maximum pooling. The function of the pooling layer 26 is to reduce the size of feature maps obtained from the mlpconv layer 152, and to concentrate and retain features in the reduced feature map. Generally, the function of the pooling layer 26 can be seen as extracting important features from the feature map, thereby emphasizing important features. In some embodiments, the maximum pooling layer 26 may also be replaced with an average pooling layer architecture.

In an embodiment, each mlpconv layer 152 and global average pooling layer 154 comprise an activation function 24, respectively. The activation function 24 can be used to regulate the output of the mlpconv layer 152 or global average pooling layer 154 to make the output non-linear, thereby increasing the prediction ability of the model. The activation function 24 may be a Saturated Activation function or Non-saturate Activation function. When the activation function 24 is a Saturated Activation function, the activation function 24 may employ an architecture such as tanh and sigmoid. When the activation function 24 is a Non-saturate Activation function, the activation function 24 may employ a Rectified Linear Unit (ReLU) or its varying architecture (for example, ELU, Leaky ReLU, PReLU, RReLU or its varying architecture). In a preferred embodiment, the activation function 24 of the mlpconv layer 152 is a ReLU architecture, and the activation function 24 of the global average pooling layer 154 is an architecture other than ReLU.

In one embodiment, the function of the global average pooling layer 154 is to reduce the dimension of the feature map obtained from mlpconv layer 152, thereby representing each feature map by an average value. In general, the effect of the global average pooling layer 154 can be seen as extracting important features from the feature map.

In an embodiment, the loss function layer 156 is used to balance the possibility prediction, that is, making possibility of two output results of the feature path similar, and thus prevent the model for training or the deep convolution neural network model 15 from applying numerous predictions to single output result.

In an embodiment, the content of aforementioned deep convolution neural network model 15 or model for training may be implemented by a programming language, Python 3.6.4, and the deep learning frame, Tensorflow, of a deep learning module, Keras 2.1.3. However, the present invention is not limited thereto.

Figure 2:
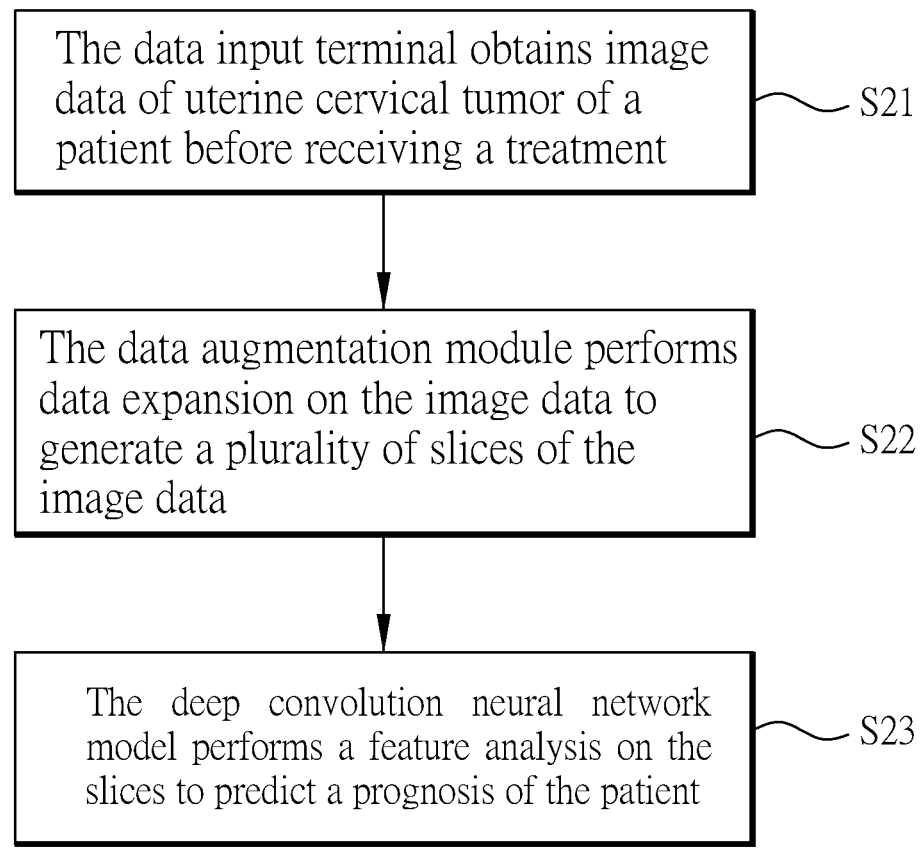
FIG. 2 is a flow chart showing the basic steps of a method of deep learning of tumor image-aided prediction of prognosis for patients with uterine cervical cancer system according to an embodiment of the present invention.

The basic operation of the present invention will be described. FIG. 2 is a flow chart showing the basic steps of a method of deep learning system of tumor image-aided prediction of prognosis for patients with uterine cervical cancer according to an embodiment of the present invention. This method is performed by the prediction system 1 in FIGS. 1(A) and 1(B), and the deep convolution neural network model 15 has finished its training process. As shown in FIG. 2, step S21 is firstly performed, and data input terminal 16 obtains image data before chemoradiotherapy. Afterward, step S22 is performed, and the data augmentation module 12 performs data expansion on the image data to generate a plurality of slice sets of the image data. Thereafter, step S23 is performed, the deep convolution neural network model 15 performs a feature analysis on the slices to predict the prognosis (i.e. the possibility of recurrence or metastasis). The details of each step will be explained below.

In step S21, a system user (for example, a physician) can input the patient's image data (including a SUVmax pixel of the tumor in the PET image) into the prediction system 1. In an embodiment, the image data will be focused on the tumor area showing an abnormal metabolic response to the tracer (for example, 18F-FDG). In an embodiment, the image data may have a plurality of voxel, and the pixel value of each voxel refers to a standardized uptake value (SUV) of glucose.

Figure 3A:
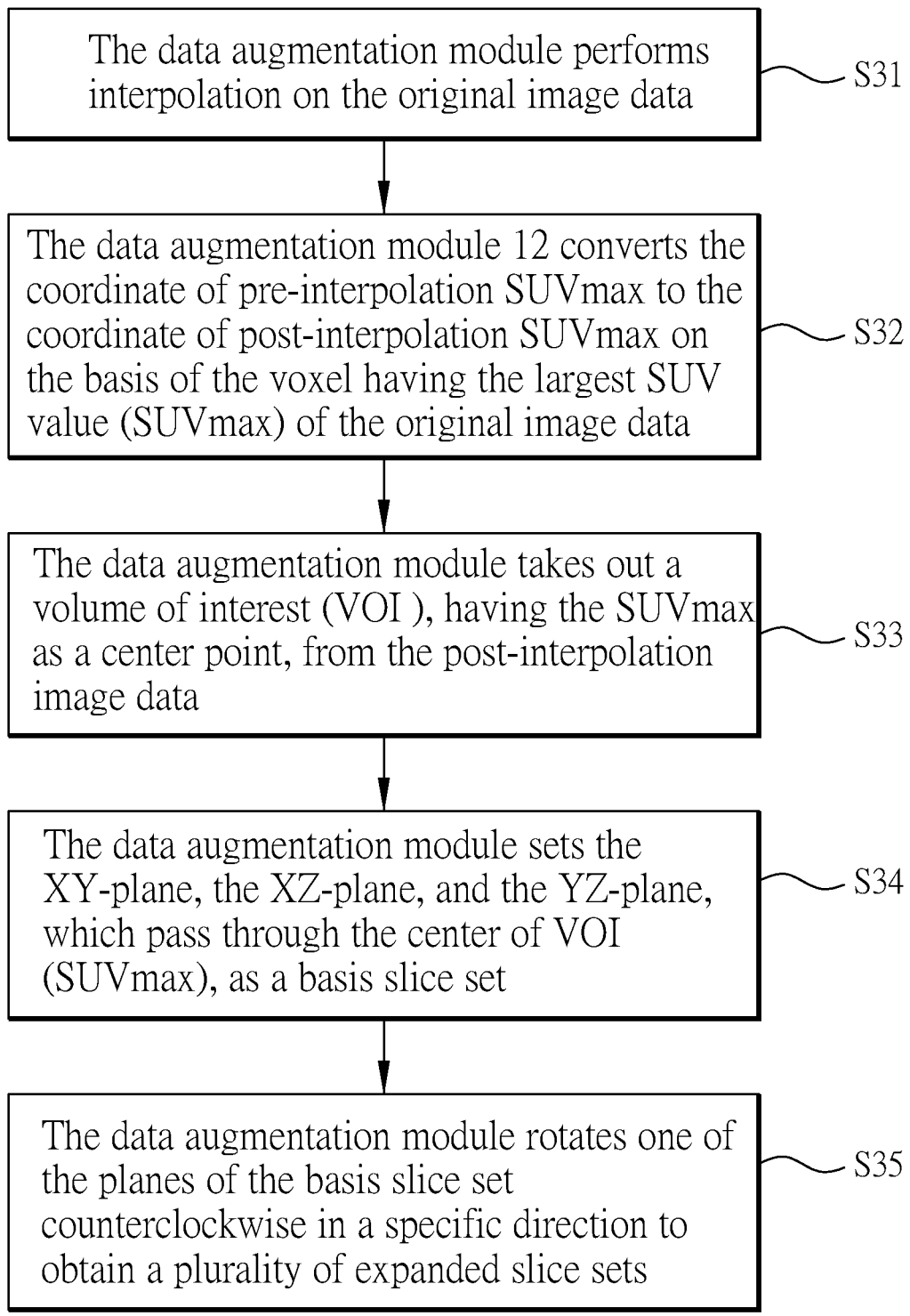
FIG. 3(A) is a flow chart of a data expansion process according to an embodiment of the present invention.

In step S22, when patient's image data is input into the prediction system 1, the microprocessor of the prediction system 1 can function according to the instruction of the computer program product 20, that is, the prediction system 1 can perform a data expansion process on the image data by data augmentation module 12. The purpose of step S22 will function if the prediction system 1 will not meet the expectation particularly when the available data are limited. Thus, there is a need to expand the data amount before training. The details of the data expansion process will be explained below, together with FIG. 3(A). FIG. 3(A) is a flow chart of a data expansion process according to an embodiment of the present invention, the data expansion process is performed by the data augmentation module 12, and the entire process can be implemented by the execution of the microprocessor in the prediction system 1.

Data Expansion Process

As step S31 is initiated, the data augmentation module 12 performs interpolation on the image data (defined as the original image data) and inputs to the prediction system 1. The purpose of this step is to increase the resolution of the image data. In an embodiment, the size of the voxel in the image data can be 5.47 mm×5.47 mm×3.27 mm, and the size of each volume pixel in the image data can be 2.5 mm×2.5 mm×2.5 mm after interpolation. Accordingly, the resolution of the image can be improved. In some cases, the size of each voxel in the image data is adjusted to 2.5 mm×2.5 mm×2.5 mm, and it is very suitable for the subsequent image processing of this system 1. It is noted that, the size of the voxel above is merely an example and is not a limitation.

Afterward, step S32 is performed. Since the aforementioned interpolation changes the resolution of the data, the data augmentation module 12 converts the coordinate of pre-interpolation SUVmax to the coordinate of post-interpolation SUVmax on the basis of the voxel having the largest SUV value (SUVmax) of the original image data.

Figure 3B:
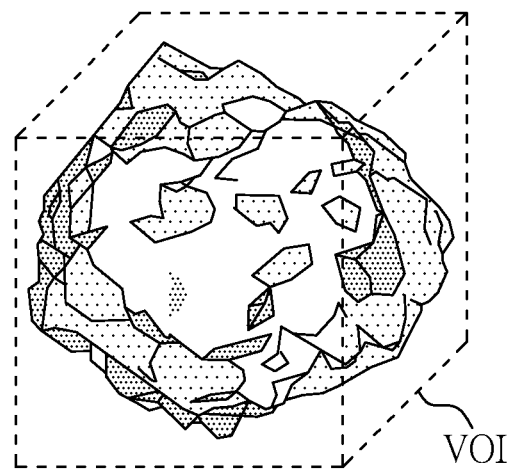
FIG. 3(B) is a schematic diagram of a volume of interest according to an embodiment of the present invention.

Then, step S33 is performed. The data augmentation module 12 takes out a volume of interest (VOI), having the SUVmax as a center point, from the post-interpolation image data. In one embodiment, the size of the VOI is set as 70 mm×70 mm×70 mm. When the size of the VOI is 70 mm×70 mm×70 mm, it can be applied to the MTV size for most uterine cervical tumors. However, the present invention is not limited. The MTV size of the uterine cervical tumor may be shown in the FIG. 3(B) exhibiting the schematic diagram of VOI according to one embodiment of the present invention.

Figure 3C:
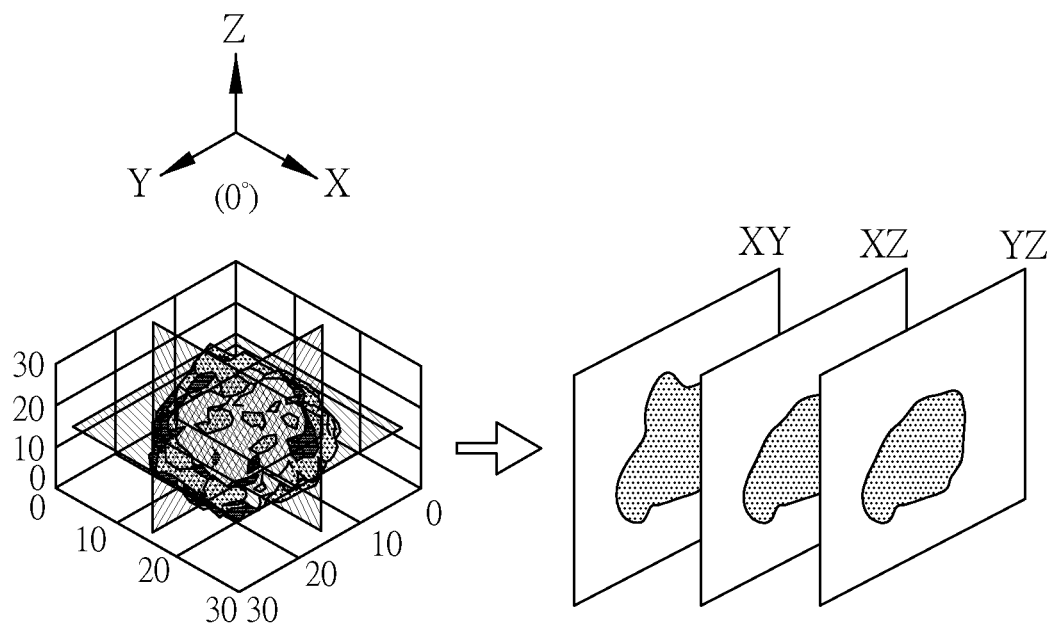
FIG. 3(C) is a schematic diagram of a basis slice set according to an embodiment of the present invention.

Thereafter, step S34 is performed. As shown in FIG. 3(C), the data augmentation module 12 sets the XY-plane, the XZ-plane, and the YZ-plane, which pass through the center of VOI (SUVmax), as a basis slice set. FIG. 3(C) is a schematic diagram for a basis slice set with non-rotated coordinate according to an embodiment of the present invention.

Figure 3D:
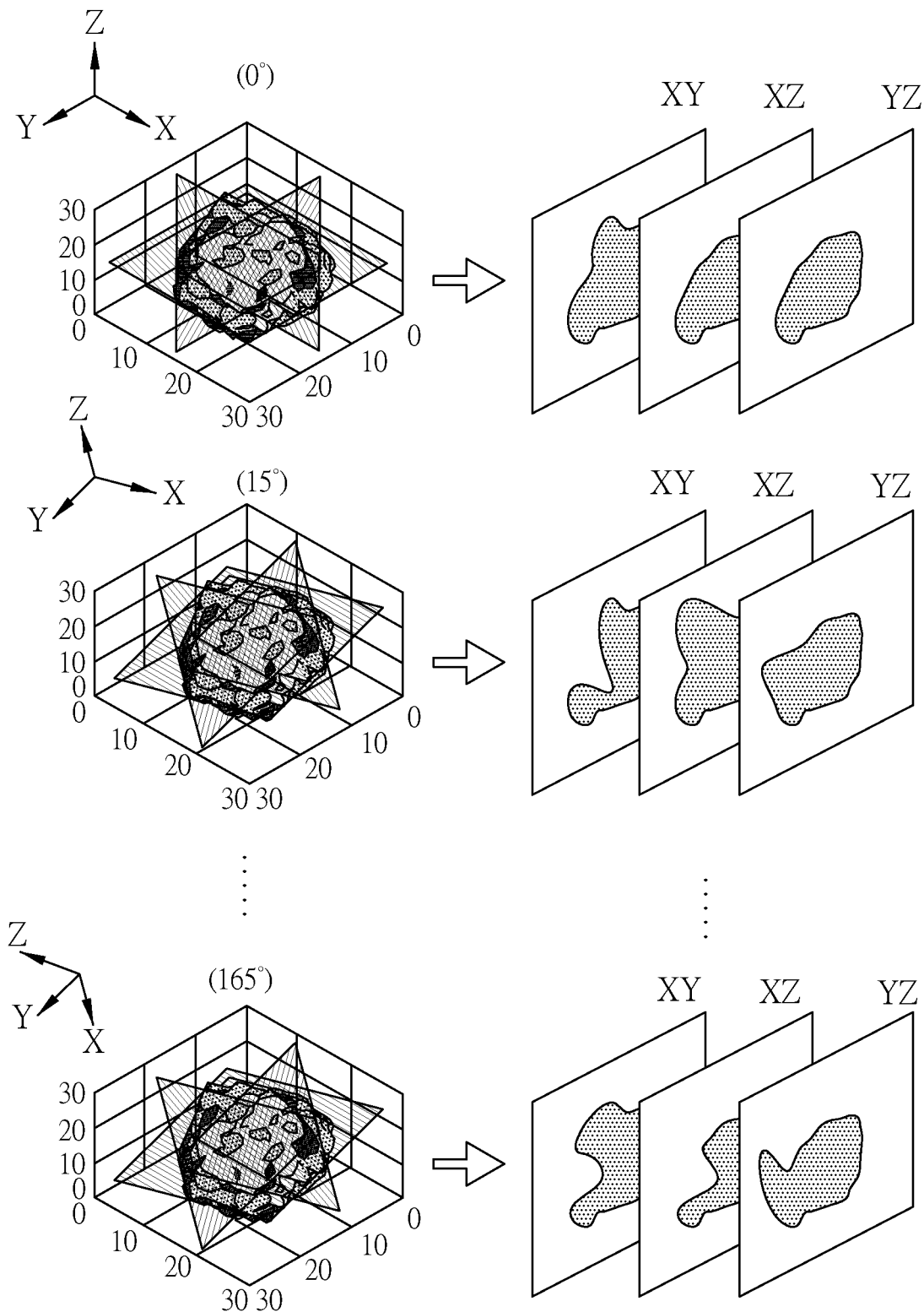
FIG. 3(D) is a schematic diagram of expanded slice sets according to an embodiment of the present invention.

Afterward, step S35 is performed. The data augmentation module 12 rotates one of the planes of the basis slice set counterclockwise in a specific direction to obtain a plurality of expanded slice sets. In an embodiment, the data augmentation module 12 rotates the XY-planes of the basis slice set counterclockwise in a specific direction, but is not limited thereto. In an embodiment, the data augmentation module 12 rotates one of the planes of the basis slice set counterclockwise in the Y-axis direction, but is not limited thereto. In one embodiment, rotating plane counterclockwise refers to rotating one of the planes of the basis slice set by 15°, 30°, 45°, 60°, 75°, 105°, 120°, 135°, 150° and 165° in a specific direction, thereby obtaining 10 rotated slice sets (i.e., expanded slice sets), as shown in FIG. 3(D). FIG. 3(D) is a schematic diagram for expanded slice sets according to an embodiment of the present invention. In one embodiment, a single image data can generate 11 slice sets (1 basis slice set and 10 rotated slice sets, wherein each slice set may comprise 3 slices), and thus the number of data will be greatly increased. As a result, the local features of the tumor images will become more obvious. In the present invention, each of slices is a two-dimensional image, so the subsequent convolution operation processes the two-dimensional image specifically. However, in another embodiment, the slices may also be three-dimensional images, and the convolution operation processes the three-dimensional image specifically. The data expansion process can be completed by the aforementioned step, and the data augmentation module 12 can generate a plurality of slice sets from a single image datum.

Please refer to FIG. 2 again. In step S23, after obtaining a plurality slices, the deep convolution neural network model 15 can analyze such slices. Since each of the slices comprises local features of the tumor, the deep convolution neural network model 15 can analyze the local features of the tumor in such slices automatically, and determine the output results of such slices through the feature paths, thereby predicting patient's prognosis (possibility for recurrence/metastasis).

Thereby, the prediction system 1 can predict a patient's prognosis before definitive chemoradiotherapy to assist the user (for example, physician) in judging whether the therapy should be adopted.

The deep convolution neural network model 15 should undergo training with deep learning in order to achieve the effect of the step S23. The details of process and method of establishing the deep convolution neural network model 15 will be elaborated as follows.

Method for Establishing the Deep Convolution Neural Network Model 115

To establish the deep convolution neural network model 15, a model for training should be trained by a plurality of image data, so that the model for training can identify features from the image data to establish a feature path. The training result (feature path) has a similar effect as human neural network, the model for training should undergo training for several times. The model for training performs a convolution operation by a feature detector and image data during each training process. The feature detector used for the first time is generated randomly, and thus different feature paths may be generated during each training process. Then, the prediction system 1 verifies the accuracy of each feature path, and sets the feature path having the highest accuracy as the path of the deep convolution neural network model 15. The following paragraphs are some key points of the establishment of the deep convolution neural network model 15 of the present invention.

Key Points for Establishing the Deep Convolution Neural Network Mode 115

1. Architecture of the Model for Training

In the present invention, the model for training employs the same architecture during each training process, and the difference is that the feature detector is randomly generated during each training process. The basic architecture of the model for training should be set up before the training process begins. In the present embodiment, each model for training comprises three mlpconv layers, one global average pooling layer and one loss function layer, wherein each mlpconv layer respectively comprises at least one randomly generated feature detector. The above model for training is a preferred example, and the present invention is not limited thereto.

2. Training Purpose

In the present invention, "training" refers to a process that the model for training automatically analyzes image data by pre-written algorithm to establish feature paths. And the "training purpose" is to identify determinant features from the large data and establish feature paths. Accordingly, a feature path with the best accuracy can be obtained. The model for training will establish a feature path after each training process, and each feature path corresponds to two output results: good or poor prognosis.

3. Number of Training

In the present invention, the overall training number of the model for training is set as 500 times. Therefore, it substantially generates 500 different feature paths after the model for training has finished all training processes. It is noted that, the number of training above is a preferred example, and the present invention is not limited thereto.

4. Number of Data

In the present embodiment, 142 patient's PET images of the uterine cervical tumor are used as original image data, 121 of the 142 patient's PET images have no PET image with local recurrence after treatment, and 21 of the 142 patient's PET images have PET images with local recurrence after treatment. It is noted that, the number of the image data above is a preferred example, and the present invention is not limited thereto. In addition, the content of the image data may vary according to the category of the prognosis. For instance, the PET image data use prognosis data relating to tumor recurrence in order to predict tumor recurrence, use prognosis data relating to tumor metastasis in order to predict tumor metastasis, and so on.

5. Data Expansion

In the present embodiment, each PET image can be expanded to 11 slice sets through the data augmentation module 12. As a result, it will generate 1562 slice sets (each set comprises 3 slices). The illustration of FIG. 3(A) can be applied to each data expansion method of each PET image, and thus the description will be omitted herein.

6. Data Distribution

During each training process, the 1562 slice sets will undergo a random distribution and will be distributed into a test group and a training group. In one embodiment, "random distribution" refers to randomly allocate the 142 PET images into 10 data strings, each data string has similar number of PET images of good and poor prognosis, and one of the data strings is set as a test group, other strings are merged as a training group. In one embodiment, the data augmentation module 12 starts the data expansion after the allocation of the test group and training group is finished, but is not limited thereto. Next, the details of the "test group" and the "training group" will be elaborated as follows. After the model for training has finished its training (for example, 500 times of the training), the "test group" is the image data used to test the accuracy of said model for training. In an embodiment, each data string is used as a test group for one time, the remaining strings are merged as a test group. The accuracy, established after each training process, of the model for training is determined by the test results of the test group, followed by summarizing such 10 test results to determine the accuracy. The method for testing the accuracy is only an example and is not limited thereto. The "training group" is image data used to train the model for training in the training phase. In one embodiment, the data of the training group may be divided into a sub-training group and a sub-verification group. The "sub-training group" is used as training data for the model for training to generate a preliminary feature path. The "sub-verification group" is used for the model for training to decide whether to adjust the verification data of the preliminary feature path, and the final feature path, which has been adjusted, is the feature path established by each of the training. In an embodiment, the ratio of number of the sub-training group and the sub-verification group is 8:2. The above is only an example and the present invention is not limited thereto. In one embodiment, the data of the training group may not be divided into a sub-training group and a sub-verification group.

7. Training and Test

Please refer to FIG. 1(A) again. In one embodiment, when the model for training undergoes training, the prediction system 1 will know the prognosis corresponding to the image data in the training group in advance, and thus the model for training can analyze and summarize possible features corresponding to the prognosis. When testing the accuracy of the model for training (which has already finished its training), the model for training will not know the prognosis corresponding to the image data in the test group in advance; after the model for training finishes the analysis and obtains results, the prognosis corresponding to the image data in the test group will be used for comparison to determine the accuracy of the test module. In an embodiment, a model with the highest prediction accuracy will be set as the deep convolution neural network model 15 by the prediction system 1, and thus the training module can form the deep convolution neural network model 15. The above is only an example and the present invention is not limited thereto.

Details of the Establishment Process of the Deep Convolution Neural Network Model 15

Figure 4:
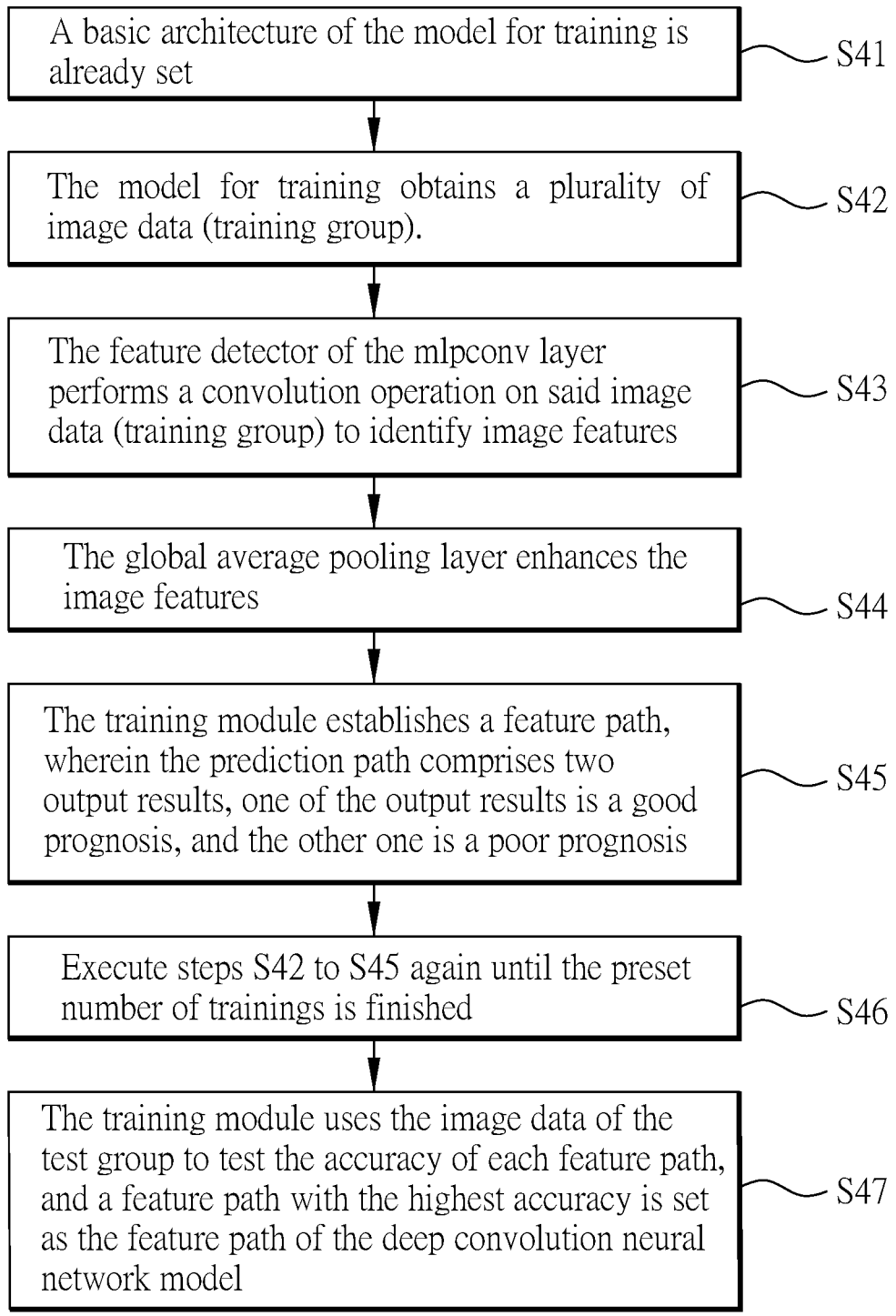
FIG. 4 is a flow chart showing the establishment of a deep convolution neural network model according to an embodiment of the present invention.

FIG. 4 is a flow chart showing the establishment of a deep convolution neural network model 15 according to an embodiment of the present invention, wherein the steps S41 to S46 correspond to a "training phase", and the step S47 corresponds to a "test phase". Please refer to the FIGS. 1(A), 1(B) and 4. Firstly, the step S41 is performed, a basic architecture of the model for training is already set, that is, numbers of mlpconv layer, global average pooling layer and loss function layer are already set, wherein the initial feature detector in the mlpconv layer is randomly generated. Afterward, the step S42 is performed and the model for training obtains a plurality of image data (training group). Then, the step S43 is performed, the above feature detector of the mlpconv layer performs a convolution operation on the image data (training group) to identify image features. Thereafter, the step S44 is performed and the global average pooling layer enhances the image features. The step S45 is then performed and the training module establishes a feature path, wherein the prediction path comprises two output results. One of the output results is a good prognosis, and the other one is a poor prognosis. Afterward, the step S46 is performed to execute steps S42 to S45 again until the preset number of trainings is finished (for example, 500 times). Then the step S47 is performed, the prediction system 1 uses the image data of the test group to test the accuracy of each feature path, and a feature path with the highest accuracy is set as the feature path of the deep convolution neural network model 15. The details of each step will be elaborated hereinafter.

Since descriptions in the previous paragraphs can be applied to the steps S41, S42, S46, and S47, the details thereof are omitted herein.

Figure 5:
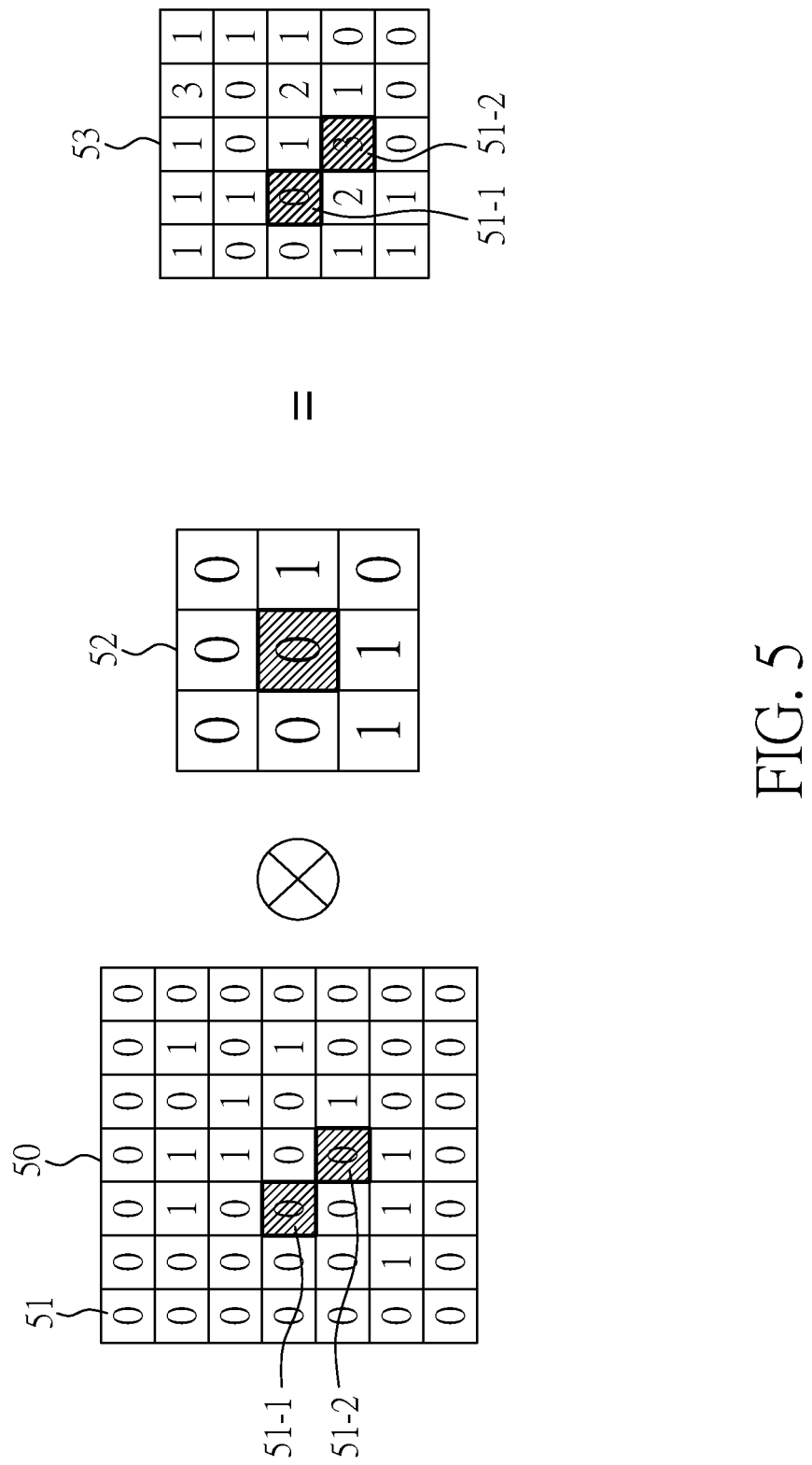
FIG. 5 is a schematic diagram showing an example of a convolution operation of an mlpconv layer.

In step S43, the content of the convolution operation will be explained by an example below. It is noted that this example has been simplified, and the actual operation will be more complicated. FIG. 5 is a schematic diagram showing an example of a convolution operation of an mlpconv layer. As shown in FIG. 5, a slice 50 may comprise a plurality of pixel positions 51, and each pixel position 51 has a pixel value (for example, SUV value). The slice position 50 and a feature detector 52 of the mlpconv layer 15 will undergo a convolution operation. After all pixel positions undergo a convolution operation with the feature detector 52, a feature map 53 will be generated.

Taking pixel position 51-1 for example, the position of the value "1" in the feature detector 52 corresponds to the pixel position 51-1 and its surrounding pixel positions are all "0", so the value of the pixel position 51-1 on the feature map 53 will be "0" after the convolution operation. Taking pixel position 51-2 for example, the position of the value "1" in the feature detector 52 corresponds to the pixel position 51-2 and its surrounding pixel positions are all "1", so the value of the pixel position 51-2 on the feature map 53 will be "3" after the convolution operation. In this example, since the size of the pixel detector 52 is 3×3, the partial pixel position (eg, the peripheral pixel position) in the slice 50 will be eliminated because the convolution operation cannot be performed. Therefore, the number of the pixel position of the feature map 53 is less than the number of the pixel position of the slice 50. According to the aforementioned method, features in the image data (PET image for uterine cervical tumor) can be identified when the convolution operations of the three mlpconv layers are finished.

In addition, in step S43, in one embodiment, an activation function will activate the convolution operation result of each mlpconv layer after the convolution operation of each mlpconv layer is finished, so that the convolution operation result has a nonlinear effect. In an embodiment, the activation function of each mlpconv layer is ReLu, and is not limited thereto.

In step S44, when the convolution operation is finished, the activation function may retain the partial features in the image map, remove the data other than the features, and the features may be then enhance by reducing the feature map size with pooling. In one embodiment, the activation function of the global average pooling layer can be represented by the following formula:

$$f(p) = \frac{1}{1+e^{-1*p}};$$

wherein p is the feature of the pooling result, f(p) is the activation result, and e is the exponential function. Furthermore, in an embodiment, the pooling result may be multiplied by different multiplying factors to adjust the range of the value.

In step S45, the loss function is set such that any image data is predicted to have a good or poor treatment effect in a similar possibility, ensuring the feature path will not bias either of the output results. With the execution of steps S41 to S47, the deep convolution neural network model 15 can have a feature path with the highest accuracy and can be used to predict the possibility of recurrence/metastasis of uterine cervical tumors in other patients. Once the deep convolution neural network model 15 is established, it can analyze the therapeutic effect by inputting the patient's PET image to the prediction system 1. In the present embodiment, of 142 patients with uterine cervical cancer received chemoradiotherapy, 21 of them has local recurrence (actual data), and the prediction performance established by the present invention has achieved an accuracy of 89%, a specificity of 93%, and a negative predictive value of 95% by cross-validation. In addition, among the same group of the patients above, 26 patients develop distant metastasis (actual data), and the prediction performance established by the present invention has achieved an accuracy of 87%, a specificity of 90%, and a negative predictive value of 95% by cross-validation.

In one embodiment, in the prediction system 1 for deep learning of tumor image-aided prediction of prognosis for patients with uterine cervical cancer, methods, and computer program product may at least be complemented by the content of the reference "Deep Learning for 18F-FDG PET Can Become An Excellent Fortuneteller in Patients with Advanced Uterine Cervical Cancer", but is not limited thereto.

Accordingly, the present invention of the deep learning system can expand a small number of image data by the data augmentation module instead of inputting a large number of the image data in the beginning. Furthermore, the present invention can accurately predict the possibility of recurrence/metastasis of uterine cervical tumors after chemoradiotherapy through the deep convolution neural network model trained by deep learning.

Although the present invention has been explained in relation to its preferred embodiment, it is to be understood that many other possible modifications and variations can be made without departing from the spirit and scope of the invention as hereafter claimed.

What is claimed is:

1. A prediction system used to analyze image data of a uterine cervical tumor, comprising:
   a data augmentation module, performing a data expansion process on the image data so as to generate a plurality of slice sets of the image data; and
   an analysis module, performing a feature analysis on the plurality of slice sets through a deep convolution neural network model to predict a prognosis after the treatment;
   wherein the data augmentation module performs an image interpolation on the image data, wherein the image interpolation sets an SUVmax pixel of the image data as a center to form a basis slice set, and the basis slice set is rotated in a specific direction to form a plurality of expanded slice sets.

2. The prediction system according to claim 1, wherein the deep convolution neural network model is formed by a model for training undergoing a plurality of trainings and tests, wherein the plurality of trainings and tests is to generate a plurality of different feature paths through a training module, using a plurality of image data for training to train the model for training for a plurality of times, and test an accuracy of each feature path by using a plurality of image data for test, and a feature path with the highest accuracy is set as a feature path of the deep convolution neural network model.

3. The prediction system according to claim 2, wherein the model for training orderly comprises: a plurality of mlpconv layers, at least one global average pooling layer and at least one loss function layer, and each mlpconv layer comprises a randomly generated feature detector.

4. The prediction system according to claim 3, wherein the feature detector of the first mlpconv layer and the image data for training undergo the first convolution operation during each training, and each of the feature detector of the subsequent mlpconv layer and the convolution operation result of the previous mlpconv layer undergo the second convolution operation to find a plurality of features of the image data for training.

5. A prediction method, used to analyze image data of a uterine cervical tumor, the method is performed by a prediction system, and the method comprises steps of:
   performing a data expansion process on the image data through a data augmentation module so as to generate a plurality of slice sets; and
   performing a feature analysis on the plurality of slice sets through a deep convolution neural network model to predict a prognosis;

wherein the data augmentation module performs an image interpolation on the image data, wherein the image interpolation sets an SUVmax pixel of the image data as a center to form a basis slice set, and the basis slice set is rotated in a specific direction to form a plurality of expanded slices.

6. The prediction method according to claim 5, wherein the deep convolution neural network model is formed by a model for training undergoing a plurality of trainings and tests, wherein the plurality of trainings and tests comprise steps of:
generating a plurality of different feature paths through a training module, which uses a plurality of image data for training to train the model for training for a plurality of times;
testing an accuracy of each feature path through the training module, which uses a plurality of image data for test; and
setting a feature path with the highest accuracy as a feature path of the deep convolution neural network model through the training module.

7. The prediction method according to claim 6, wherein the model for training orderly comprises: a plurality of mlpconv layers, at least one global average pooling layer and at least one loss function layer, and each mlpconv layer comprises a randomly generated feature detector.

8. The prediction method according to claim 7, wherein the feature detector of the first mlpconv layer and the image data for training undergo the first convolution operation during each training, and each of the feature detector of the subsequent mlpconv layer and the convolution operation result of the previous mlpconv layer undergo the second convolution operation to find a plurality of features of the image data for training.

9. A computer program product stored in a non-transitory computer-readable medium for the operation of a prediction system, wherein the prediction system is used to analyze image data of a uterine cervical tumor, wherein the computer program product comprises:
an instruction, enabling the prediction system to perform a data expansion process on the image data so as to generate a plurality of slice sets; and
an instruction, enabling the prediction system to perform a feature analysis on the slice sets so as to predict a prognosis of the person after the treatment;
wherein the data expansion process comprises steps of: performing an image interpolation on the image data, wherein the image interpolation sets an SUVmax pixel of the image data as a center to form a basis slice set, and the basis slice set is rotated in a specific direction to form a plurality of expanded slices.

* * * * *